United States Patent
Palmer et al.

(10) Patent No.: US 6,344,336 B1
(45) Date of Patent: Feb. 5, 2002

(54) ASSAY APPARATUS

(75) Inventors: Derek Adeyemi Palmer, Farnborough; Martin Thomas French, Sevenoaks, both of (GB)

(73) Assignee: Kalibrant Limited, London (GB)

( * ) Notice: Subject to any disclaimer, the term of this patent is extended or adjusted under 35 U.S.C. 154(b) by 0 days.

(21) Appl. No.: 09/422,757

(22) Filed: Oct. 21, 1999

Related U.S. Application Data

(62) Division of application No. 09/125,104, filed on Aug. 6, 1998, now Pat. No. 6,159,426.

(30) Foreign Application Priority Data

Sep. 2, 1996 (GB) .............................................. 9602635

(51) Int. Cl.⁷ ................................................ G01N 33/543
(52) U.S. Cl. ................................ 435/7.1; 435/4; 435/5; 435/6; 436/501; 436/514; 436/518; 436/533; 436/534; 436/536; 436/539; 436/541
(58) Field of Search ............................. 435/4, 5, 6, 7.1; 436/501, 518, 514, 536, 533, 534, 539, 541

(56) References Cited

U.S. PATENT DOCUMENTS

| | | | |
|---|---|---|---|
| 3,896,217 A | 7/1975 | Johnson | 424/1 |
| 4,009,005 A * | 2/1977 | Johnson | 23/253 R |
| 4,039,652 A * | 8/1977 | Adams et al. | 424/1 |
| 4,059,685 A | 11/1977 | Johnson | 424/12 |
| 4,158,630 A | 6/1979 | Stearns | 210/198 |
| 4,166,102 A | 8/1979 | Johnson | 424/1 |
| 4,180,383 A | 12/1979 | Johnson | 422/69 |
| 4,277,560 A * | 7/1981 | Gray et al. | 435/7 |
| 4,456,689 A | 6/1984 | Witty et al. | 436/500 |
| 4,551,426 A * | 11/1985 | Freytag et al. | 435/7 |
| 4,707,441 A * | 11/1987 | Ahmad et al. | 435/7 |
| 4,751,004 A * | 6/1988 | Stevens et al. | 210/659 |
| 4,751,189 A * | 6/1988 | Rocklin | 436/150 |
| 4,801,726 A * | 1/1989 | Giese et al. | 556/419 |
| 5,149,661 A * | 9/1992 | Gjerde et al. | 436/533 |
| 5,183,740 A * | 2/1993 | Ligler et al. | 435/7.32 |
| 5,372,783 A | 12/1994 | Lackie | 422/68.1 |
| 5,389,523 A * | 2/1995 | Plant et al. | 435/7.92 |
| 5,393,673 A * | 2/1995 | Gjerde | 436/171 |
| 5,554,340 A | 9/1996 | Lackie | 422/68.1 |
| 5,879,881 A * | 3/1999 | Rubenstein | 435/5 |

FOREIGN PATENT DOCUMENTS

| | | | |
|---|---|---|---|
| EP | 0 030 087 | 6/1981 | |
| JP | 3-206963 (a) | 9/1991 | 33/544 |

\* cited by examiner

Primary Examiner—Christopher L. Chin
(74) Attorney, Agent, or Firm—Heslin Rothenberg Farley & Mesiti P.C.; Candice J. Clement

(57) ABSTRACT

The present invention relates to an assay apparatus for detecting a product in a sample. The assay apparatus comprises a fluid pathway with an input of the sample and an input for a reagent with a detectable moiety which transports the sample to a detecting means via a barrier arranged to prevent a product-reagent complex passage but allow passage of unbound reagent and sample. The apparatus also includes supply means for supplying a substance adapted to breakdown the complex into a detectable moiety which can flow through the barrier to the detecting means.

5 Claims, 3 Drawing Sheets

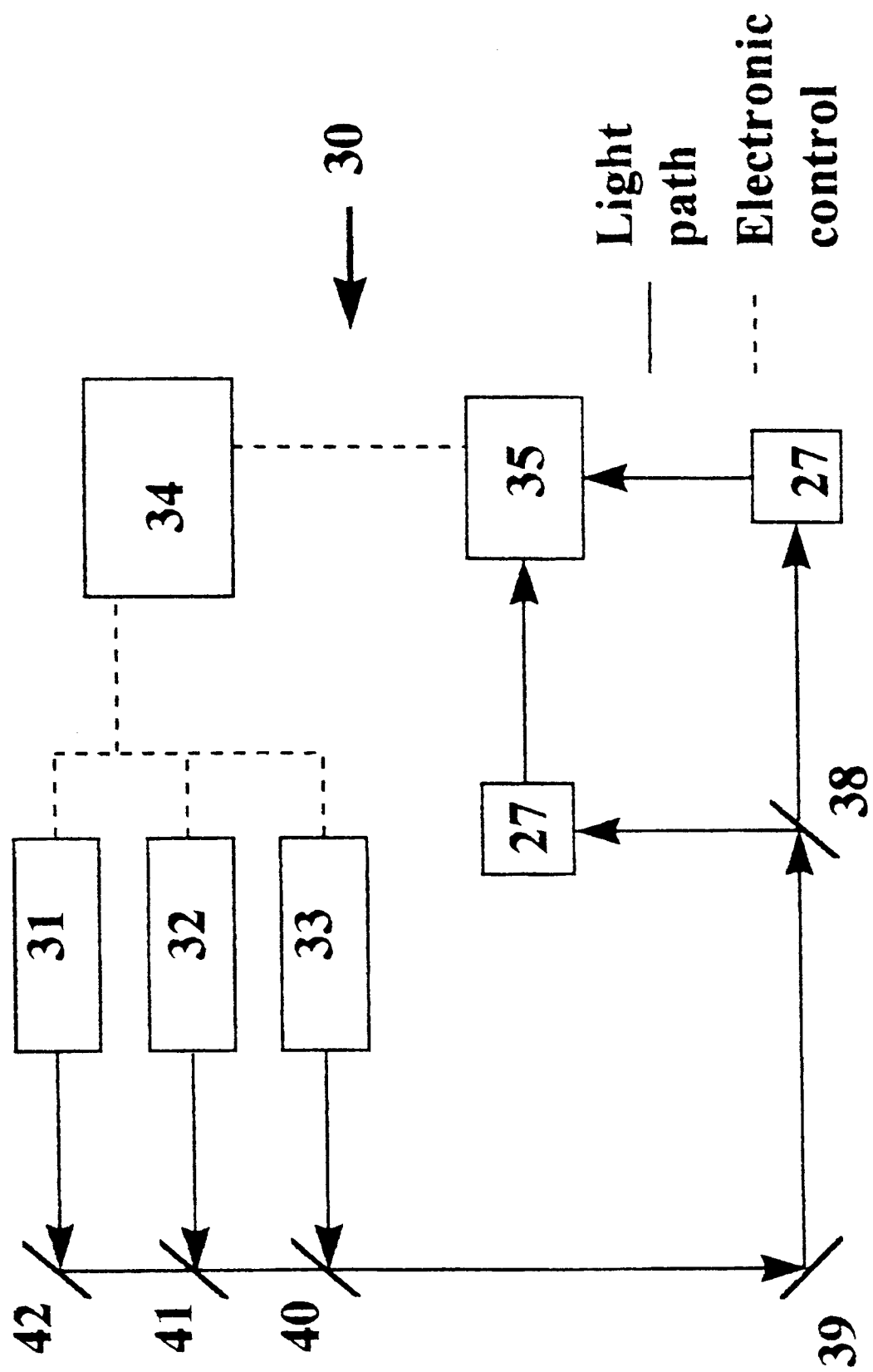

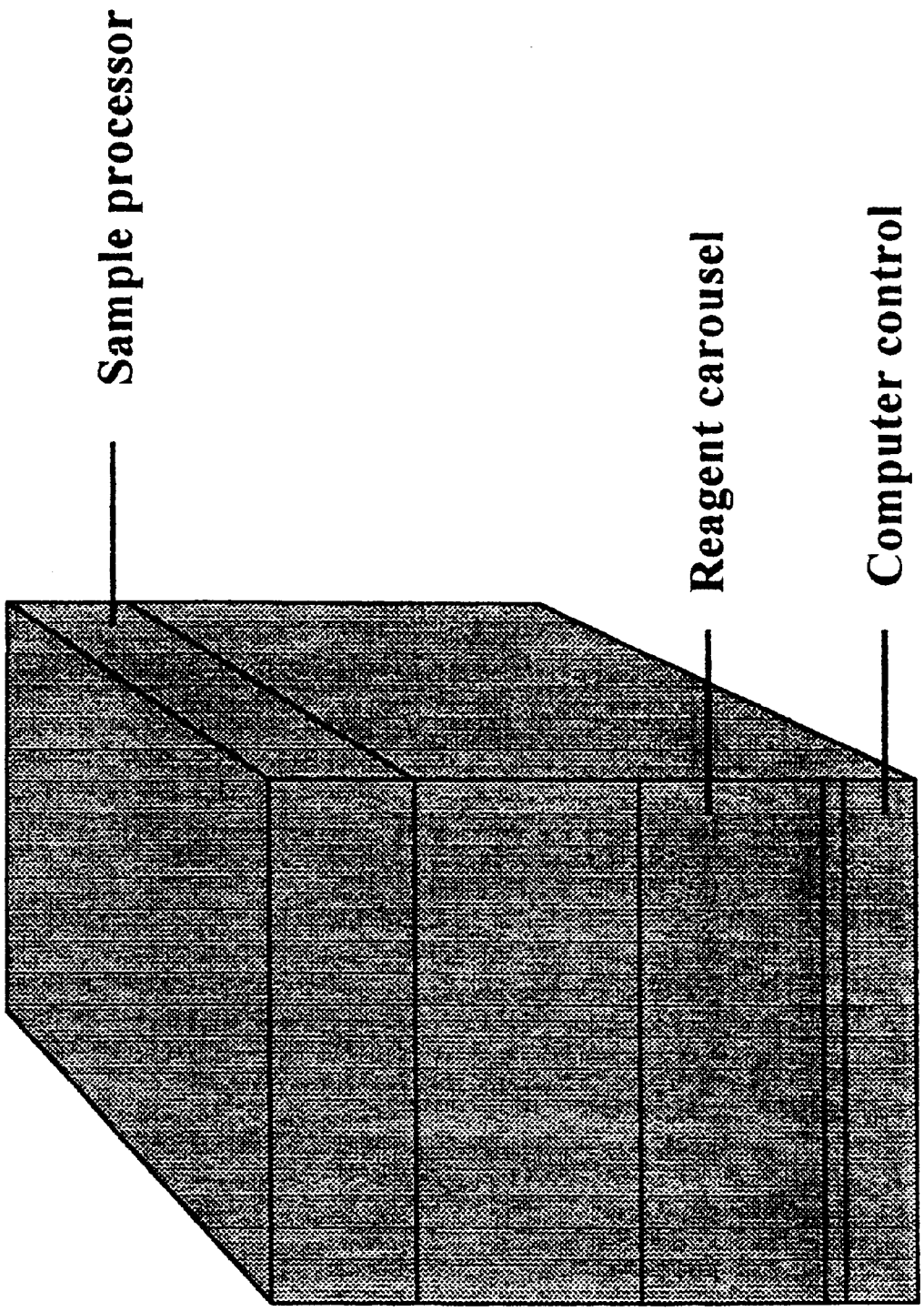

ASSAY APPARATUS

CROSS REFERENCES TO RELATED APPLICATIONS

This application is a division of U.S. patent application Ser. No. 09/125,104 (now U.S. Pat. No. 6,159,426), filed Aug. 6, 1998, now U.S. Pat. No. 6,150,426 as a §371 filing of PCT/GB97/00334, filed Feb. 6, 1997, and claims priority from GB Patent Application Number 9602635.6, filed Feb. 9, 1996. The entire disclosures of the earlier applications are incorporated herein by reference.

FIELD OF THE INVENTION

The present invention relates to a method of performing assays and apparatus therefor, in particular but not exclusively to a method and apparatus for immunoassays.

BACKGROUND OF THE INVENTION

It is well known to perform assays where aliquots of a sample are tested to see if the sample contains a particular substance by reaction with one or more reagents to form a complex such as an antigen/antibody complex which may then be detected.

A great number of different techniques exist for performing assays and the instances in which assay techniques are used are becoming more widespread. An overview of currently used techniques is given in the article "Update on immunoassay automation" Proc. UK NEQAS Meeting 1994:1:163–170; Wheeler, Michael J. For example, various types of immunoassays are now commonly used to test blood and other samples for a great number of different compounds. Yet, even a large hospital would not have a large number of different assay machines and so the apparatus must be capable of performing a range of different tests on different samples. The versatility of any assay technique must necessarily increase as the number of tests that can be requested on samples increases. The growing desire that assays can be performed directly in places such as Doctors Surgery's, rather than sending the samples away for analysis by a laboratory in a hospital further increases the demand for versatile machinery.

In conjunction with the growth of the assay systems, it has become necessary that any particular assay is performed ever more precisely. The importance of the accuracy of the test will be apparent, as, for example, a patient's treatment may be determined based on the result of the assay and so an inaccurate result may lead to inappropriate treatment of the patient.

The growth in assay techniques being used has led to a large number of systems on the market. Presently, most systems are semi-automated or automated systems, where after loading of the reagents and samples no further input is required from a human operator, unless a breakdown occurs.

As will be apparent from the aforementioned article by Wheeler, the majority of the devices presently on the market comprise a loading tray for loading multiple samples, for example between 20 and 100 samples, which are not necessarily of the same nature or having the same assay performed on them. There is also a reagent input tray which holds a number of reagent cartridges for the various different tests to be performed. In the machine the samples are transferred, normally by pipetting into an assay cell where the sample is combined with the necessary reagent or reagents. The assay cell is then transferred to a part of a machine where it can be held for sufficient time for the reagent and the sample to combine. Thereafter the sample cell is transferred to the detector which detects the presence of a known indicator to determine whether or not the sample contained a particular component and/or how much of that component was present in the assay. Normally a robotic arm is used for transferring the assay cell around the machine, for example from the loading area to the wash station, to the waiting area and onward to the detector. Whilst assay apparatus of this type can offer semi-automated functioning, problems do occur due to the mechanical movement of the samples. Furthermore, it is necessary to have pipettes with replaceable pipette tips or other means to ensure that one sample does not contaminate another sample when being. As each sample cell must be incubated with the appropriate reagents, a relatively large number of sample cells may have to be incubated at any one time and thus the size of the machine remains relatively large due to the space required for the waiting area.

Recently, it has been suggested to use flow injection technology in assay equipment. A review of this technology is given in an article by Puchades, R. et al "A Comprehensive Overview on the Application of Flow Injection Techniques in Immunoanalysis, Critical Reviews in Analytical Chemistry" 23,(4):301–321(1992). The fundamental difference between this technology and the above described systems is that the samples and the reagents are combined in a fluid stream, which extends to the detector. This dispenses with the need of sample cells and generally reduces the mechanical components of the system.

WO94/03104 discloses a flow injection technique with developments shown in WO94/20855 and WO95/22766. In this known flow injection technique, samples and reagents are again loaded into the machine. These are combined in the fluid stream. The fluid stream then passes along a conduit which has a transparent portion. In the transparent portion a screen is produced of small, preferably magnetic, beads. As the fluid stream carries these samples and reagents into the area of the screen, complexes of the reagent-sample are held by the screen. Normally, a second set of transparent beads are covered with a bound reagent complex which allows a competition assay to occur in this region. Quantitative analysis of the presence of a product in the sample is conducted by electro-magnetic detection means, e.g. fluorometer, at this point which is why the beads and the section of the conduit must be transparent in this area. This technique is particularly suitable for measuring the rates and progress of the assay reaction.

Clearly, in this known flow injection method the detection means and the transparent area of the conduit must be in close physical proximity and it is suggested that the transparent part of the conduit is formed as part of the lens system of the detector means. This leads to a complex arrangement of the machinery which limits the types of assays which can be performed by this technique.

The present invention seeks to provide an improved assay system which is simple, reliable and versatile.

SUMMARY OF THE INVENTION

According to a first aspect of the present invention there is provided an assay apparatus for detecting a product in a sample, comprising a fluid pathway with an input for the sample and an input for a reagent with a detectable moiety which transports the sample to a detecting means via a barrier arranged to prevent a product-reagent complex passage but allow passage to the reagent and the sample, where the complex is formed through interaction of the reagent and any of the product in the sample, wherein the apparatus also includes supply means for supplying a substance adapted to breakdown the complex into a detectable moiety which can flow through the barrier to the detecting means.

According to a second aspect of the present invention there is provided an assay method for detecting a product in a sample, comprising the steps of:

a) feeding the sample and a reagent with a detectable moiety into a fluid pathway;

b) allowing the sample and reagent to interact to form a mixture of the sample, the reagent and a product-reagent complex if the product is contained in the sample;

c) holding the complex at a barrier across the fluid pathway which barrier allows any uncomplexed sample and/or reagent to flow therethrough;

d) subsequently breaking down the complex into a detectable moiety which can flow through the barrier, for example the reagent;

e) detecting the presence of any detectable moiety released in step d) downstream of the barrier.

The present invention thus provides a flow injection assay system where the detector means is located downstream of where the reagent sample complex is formed. This provides a simplified system. In this arrangement a greater range of assays can be performed compared with the previously known flow injection techniques. This is clearly advantageous and is due to the fact that the analysis is not performed at the screen.

In preferred embodiments of the invention there is provided that the inputs are arranged to input a series of spaced apart aliquots containing a sample and respective reagents in to the fluid pathway, the apparatus further including a plurality of incubation loops, each loop being individually isolatable from the fluid pathway by loop-valve means, wherein each aliquot in the fluid pathway is directed into a selected loop for a known period. This allows a particularly compact way of processing several samples at the same time, yet as there are no assay cells, the apparatus remains compact. Preferably, the loop-valve means comprises a single valve arranged to allow at most one selected incubation loop to form part of the fluid pathway at any given time. This provides a simple way of ensuring that each sample travels the same distance compared to linearly spaced valves for each loop.

Normally, a detection pathway forms the fluid pathway downstream of the barrier, the detection pathway including waste-valve means arranged to direct fluid in the detection pathway to either an outlet or past the detector means which prevents the uncompleted mixture from contaminating the flow cell.

Preferably, the fluid pathway is divided into a plurality of the said detection pathways with splitter-valve means arranged to direct each respective aliquot into a respective selected one of the detection pathways. The multiple pathways may extend from any point after the incubation loops. This improves the capacity of the apparatus as one pathway can be washed whilst another is analysing a sample.

Advantageously, one detector comprises the detection means for all the detection pathways.

BRIEF DESCRIPTION OF THE DRAWINGS

A preferred embodiment of the invention will now be described with reference to the accompanying drawings in which:

FIG. 2: shows a detector for use in the apparatus of FIG. 1; and

FIG. 3: depicts the overall construction of the apparatus of FIG. 1.

DETAILED DESCRIPTION OF PREFERRED EMBODIMENT

Figure 1:
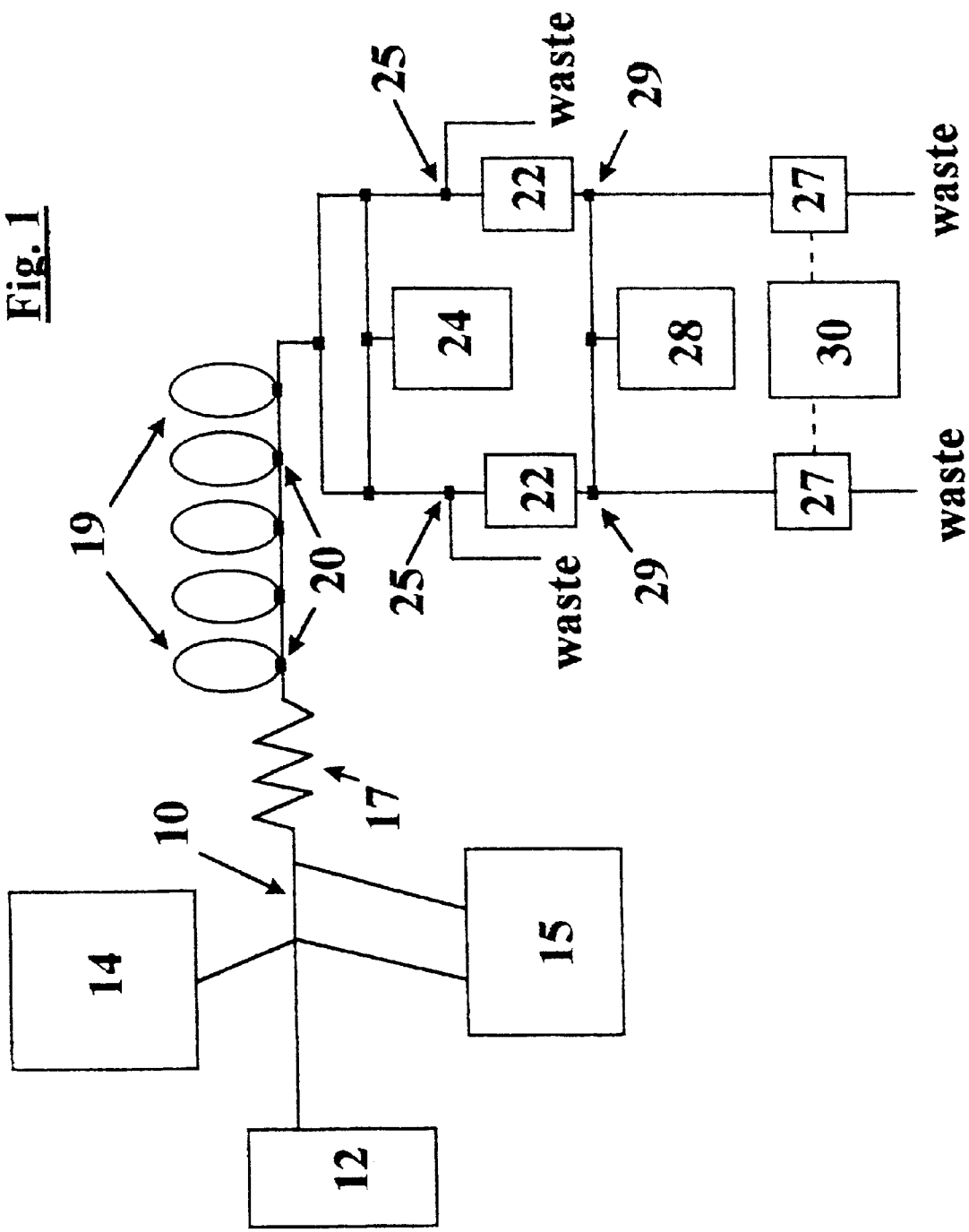
FIG. 1: shows a schematic representation of an assay apparatus according to the present invention.

FIG. 1 shows a flow injection immunoassay analyser as an integrated system. The system operates using the principles of flow injection analysis, that is a continuous stream of liquid is used to transport discrete volumes of sample or reagents that are injected into the stream. These materials can then be brought into contact with one another or with other materials that may be in solution or fixed to a surface so that they interact in a way that can be measured and thus the flow injection process is directly analogous to the manipulations that take place in traditional immunoassays using microtiter plates or tubes except that injection loops or syringes and precise control of flow rate replace the use of pipettes, washers and shakers.

A carrier buffer stream is generated from run buffer 12. A plurality of samples are held in a sample processing unit 14 which also prepares each sample for analysis. Analysis for a particular target molecule (a product) takes place by injecting a known volume of a sample that possibly contains the product, into the carrier buffer stream and mixing it with reagents from a reagent cartridge 15.

The sample processor unit 14 has the capacity to hold approximately 100 samples and a normal variety of tube sizes. The unit 14 is capable of carrying out accurate and precise pipetting to generate a sample dilution as required. This may be in a traditional manner with appropriate volumes transferred to a separate tube on the processor bed or by using the flow system where a fixed volume of sample and a variable volume of diluent (or vice versa) are merged in a mixing coil before a fixed volume is taken for analysis. The unit 14 may employ robot arm (not shown) carrying a sample probe (not shown). The robot arm would normally be capable of movement in three planes and the probe can be washed between sample manipulations at an on board wash station. Samples can be loaded onto the processor unit 14, preferably in their original tubes, of varying dimensions, in pre-prepared racks of tubes or in pre-prepared microtiter plates. Sample identification and tracking is made possible through bar codes which may be placed on the individual tubes, or the tube racks or the microtiter plates and the bar codes are read by the on board bar code reader, though other tracking systems can be used.

The flow system of the instrument consists of transmission tubing 10 made from chemically and biologically inert material such as commercially available nylon or PEEK with an inner diameter of typically 0.8 mm, although this may change to suit the circumstances. The pumping system (not shown) consists of several low pressure pumps, most likely peristaltic pumps which may be of differing size, sophistication and performance and will be capable of delivering a highly reliable flow rate. A central pump will he used to move the carrier buffer, samples and reagents through the system whilst other pumps which are likely to be less sophisticated, will be used to carry out other manipulations, such as reagent transport, barrier washing and conjugate elution. The operation of each pump will be controlled by the central computer (not shown) to ensure optimum performance and effective synchronisation. The computer will also have control over the many automated switching valves (described in more detail hereinafter), which at the appropriate times direct samples or reagents into or out of the main carrier stream. These valves may be electronically or pneumatically operated and must be extremely reliable and robust as they will-be used many times in any working day. They will be very simple in design needing only to switch the liquid flow between one of two channels or limited number of inert surfaces where they come into contact with the liquid stream.

Generally, the reagents required for each assay are principles are applied in each case and only two components are normally required. It is preferred for all assays to utilise micro-beads of a defined diameter and with the property of neutral density so that they remain in a cellulose material with low non-specific binding properties although other suitable materials may be preferred. The surface of these beads is coated, probably through covalent conjugation, although other procedures material such as an antibody or other compound that specifically binds only the analyte of interest in the assay. In a more sophisticated assay format, it is possible to coat two or more ligand binders with different specificity's onto the bead surface and this allows for multianalyte determination from the same sample. The second reagent is a labelled material which may be an analogue of the analyte of interest or binder with specificity for the analyte depending on the assay format required. The label is often a fluorophore with spectral characteristics that allow it to be detected in the near infra red region of the electromagnetic spectrum, however other labels such as liposomes, enzymes and chemiluminescent materials are also possible.

The fixed volumes of the reagents and the sample are mixed together in a mixing coil 17 and allowed to incubate together for a fixed time. The incubation is preferably accomplished by removing the aliquot out of the main flow stream and into one of the incubation loops 19. The access to the incubation loops 19 is controlled by valve means 20. The loop 19 is made from a fixed length of transmission tubing of an appropriate internal diameter, however the overall volume should be carefully chosen to ensure precise replication of incubation conditions. In the incubation loop, any of the product which is contained in the sample should interact with the reagent to form a complex which is bound to a microbead. The complex bound to the microbead must include a detectable moiety. After a given time the computer switches the aliquot of mixture back into the main stream and it is carried down to the membrane barrier 22 where the micro beads are retained whilst all other materials flow through and are passed to waste. The barrier 22 consists of a porous membrane made from a chemically and biologically inert material such as nylon and the barrier 22 is sized and arranged to prevent all beads from passing through to the flow cell. The pore structure of the membrane is governed by the size of the micro beads, however it is important that the membrane has a low non-specific binding of excess reagents and that substantially all (eg>95%) of the beads are retained. The flow path is then washed by a period of flow with carrier buffer to wash off any unbound reagents and possibly the flow rate is raised during this period, so the barrier 22 should have good flow properties. Subsequently, the various valves are switched in synchronisation to divert the main buffer flow from the barrier 22 whilst introducing an elution buffer from vessel 24 to flow through the barrier 22. The turning of the switch can be gauged from monitoring the unbound reagent flowing through the flow cell 27 to waste. This releases the label (detectable moiety) from the microbead to flow through the barrier 22. The flow is now directed to a flow cell 27 for measurement downstream. The flow cell 27 is likely to be a quartz silica cylinder, although other materials and shapes may be preferred, with a total volume unlikely to exceed 200 $\mu$l and which is normally illuminated by a light source and monitored by a detector 30 as explained in more detail below. Following elution further valve switching allows the membrane to be back flushed with an appropriate buffer from vessel 28 which removes the beads to waste through valve 25 and cleans the membrane ready for the next sample aliquot.

The detector 30 is shown in greater detail in FIG. 2 and consists of a laser diode module 31, 32, 33, a light path of mirrors and beam splitters 38 to 42, identical duplicate flow cells 27 and a single detector 35 which will most probably be a red sensitive photomultiplier tube but could also be a silicon photodiode or other detector. The choice of lasers will be very much dependent on the available fluorophores since the lasing wavelength and optimum fluorophore excitation wavelength need to be well matched. The rate of development in the field of solid state lasers and long wavelength fluorophores is rapid and the final choice for these components cannot be made now. However it is likely that the lasers should have at least a 1 milliwatt output and operate above 550 nm, whilst the fluorophores should be water soluble, stable in solution, unaffected by pH changes, emit their fluorescence above 600 nm and have the general properties required of a good fluorophore.

The laser module 31, 32, 33 can contain more than one laser, each of which can in turn be switched into the light path whilst at the same time collecting data from the detector into a separate channel. Computer control of this switching allows the potential for multi-label detection by operating 2 or more carefully chosen lasers of different excitation wavelength in a rapid pulse mode, one after the other, and monitoring the associated emission from its paired fluorophore. In this way specific measurements can be made in mixtures of fluorophores and this leads to the possibility of multi analyte determinations from the same elution peak. If pairs or more of analytes are measured in this way the throughput of the instrument is greatly increased and the usage of sample greatly reduced since mixed specificity beads can be used for the sample capture.

The resulting signal is plotted as a peak and the calculated area used to determine the concentration of the sample from a curve generated from standard solutions.

The system operates in random access mode but has the in-built capacity for immediate analysis of emergency samples, which are placed in separate rack on the autosampler. The timing and scheduling of operations are precisely controlled by the software which is icon driven, intuitive to use and which operates in a Windows™ environment. The software is designed to run on a notebook type computer which can be closed and stored in the base of the instrument when not required. Communication with the instrument is bi-directional, allowing feedback from off-scale results to initiate appropriate dilution and sample re-analysis. The instrument and software are fully configured for operation within a Laboratory Information Management System (LIMS) environment, including quality control monitoring of assay controls and reagent cartridge performance.

The analyser is designed to be capable of measuring greater than 20 clinically important substances, each of which will have a dedicated cartridge of reagents, capable of approximately 200 analyses held in the reagent carousel on board the instrument. The cartridge design will ensure that reagents can be stirred if required and kept at constant temperature through control of either the carousel compartment or the cartridge itself. Each cartridge holds information about itself, possibly on a bar code.

In the illustrated embodiment there are two detector flow pathways. This is particularly advantageous as one of the two pathways can be analysing a sample whilst the other pathway is being washed from wash buffer 28 via one of the wash valves 29. This greatly increases the number of samples which can be analysed in a given time period. This design is particularly advantageous when used in conjunction with the detector of the present invention which allows for the two (or more) flow cells 27 to be analysed from a single radiation generator/emitter and so the increased capacity is provided at little extra cost.

Of course, the detector 30 can be used in other assay/analysis systems where its advantages can also be utilised. Furthermore, other types of detectors could be used other than lasers that still operate with the advantageous single detector and/or source but have several flow cells for detection of the detectable moiety.

We claim:

1. An assay method for detecting a product in a sample, said method comprising the steps of:
    a) feeding the sample and a reagent with a detectable moiety into a fluid pathway;
    b) allowing the sample and reagent to interact as they flow down the pathway, to form a mixture of the sample, the reagent and, when the product is present in the sample, a product-reagent complex, said mixture formed upstream of a barrier located within said fluid pathway and extending across a cross section thereof;
    c) flowing the mixture to said barrier, said barrier retains any product-reagent complexes formed in step b), but allows passage of uncomplexed sample and reagent therethrough;
    d) subsequently breaking down the retained complexes to release said detectable moiety for passage through the barrier; and
    e) detecting said released detectable moiety downstream of the barrier.

2. The method according to claim 1, wherein the complex is formed on a bead which is passed to waste after step d).

3. The method according to claim 1, wherein steps a) to c) are repeated for a series of separated aliquots flowing down the pathway, where in step b) each respective aliquot is directed into an incubation loop where the aliquot is isolated from the rest of the fluid pathway for a period in order for interaction of the reagent and any product in the sample to occur to form the complex.

4. The method according to claim 1, where in step c) the complex is held until the rest of the aliquot has flowed past the barrier and waste-valve means directs said rest to waste outlet, and then the waste-valve means switches to direct the detectable moiety released in step d) to the detector means.

5. The method according to claim 3, wherein there are a plurality of detection pathways downstream of the barrier, each aliquot being directed to a respective detection pathway for detecting any of the detection moiety, and the other detection pathways will be unused, undergoing a wash cycle, or analyzing a different aliquot, when the respective one detection pathway is in use.

* * * * *

UNITED STATES PATENT AND TRADEMARK OFFICE
CERTIFICATE OF CORRECTION

PATENT NO. : 6,344,336 B1  
DATED : February 5, 2002  
INVENTOR(S) : Palmer et al.

Page 1 of 1

It is certified that error appears in the above-identified patent and that said Letters Patent is hereby corrected as shown below:

<u>Column 8,</u>  
Line 10, delete "c)" and insert -- e) --

Signed and Sealed this

Fourteenth Day of May, 2002

*Attest:*

JAMES E. ROGAN  
*Attesting Officer*     *Director of the United States Patent and Trademark Office*